(12) United States Patent
Lootz et al.

(10) Patent No.: US 7,004,968 B2
(45) Date of Patent: Feb. 28, 2006

(54) STENT

(75) Inventors: Daniel Lootz, Warnemuende (DE); Karsten Koop, Rostock (DE); Frank Bakczewitz, Rostock (DE); Martin Kiekbusch, Stralsund (DE)

(73) Assignee: Biotronik GmbH & Co. KG, Berlin (DE)

( * ) Notice: Subject to any disclaimer, the term of this patent is extended or adjusted under 35 U.S.C. 154(b) by 12 days.

(21) Appl. No.: 10/739,905

(22) Filed: Dec. 17, 2003

(65) Prior Publication Data

US 2004/0172123 A1    Sep. 2, 2004

(30) Foreign Application Priority Data

Dec. 20, 2002    (DE) ................ 102 61 822

(51) Int. Cl.
*A61F 2/06* (2006.01)

(52) U.S. Cl. .................................... 623/1.15

(58) Field of Classification Search ............... 623/1.15, 623/1.22

See application file for complete search history.

(56) References Cited

U.S. PATENT DOCUMENTS

| 5,810,872 | A | | 9/1998 | Kanesaka et al. | |
|---|---|---|---|---|---|
| 5,925,061 | A | | 7/1999 | Ogi et al. | |
| 6,033,433 | A | * | 3/2000 | Ehr et al. | 623/1.16 |
| 6,090,127 | A | * | 7/2000 | Globerman | 606/194 |
| 6,117,165 | A | * | 9/2000 | Becker | 623/1.15 |
| 6,123,721 | A | * | 9/2000 | Jang | 623/1.15 |
| 6,325,821 | B1 | * | 12/2001 | Gaschino et al. | 623/1.15 |
| 6,610,086 | B1 | * | 8/2003 | Kock et al. | 623/1.22 |
| 6,749,629 | B1 | * | 6/2004 | Hong et al. | 623/1.15 |
| 6,878,162 | B1 | * | 4/2005 | Bales et al. | 623/1.15 |
| 2002/0095206 | A1 | | 7/2002 | Addonizio et al. | |

FOREIGN PATENT DOCUMENTS

| DE | 20019429 U1 | 11/2000 |
|---|---|---|
| DE | 199 52 295 | 5/2001 |
| WO | WO 99/38458 A | 8/1999 |
| WO | WO 00/02502 | 1/2000 |
| WO | WO 00/24340 | 5/2000 |
| WO | WO 00/62710 | 10/2000 |
| WO | WO 01/89414 | 11/2001 |
| WO | WO 02/26164 | 4/2002 |
| WO | WO 02/091958 A | 11/2002 |

* cited by examiner

*Primary Examiner*—(Jackie) Tan-Uyen T. Ho
(74) *Attorney, Agent, or Firm*—Hahn Loeser & Parks LLP; John J. Cunniff (57) ABSTRACT

The invention concerns a stent comprising a longitudinal axis (12) and a peripheral wall (14) which is formed at least over a part of the length of the stent (10) by a lattice-like carrier structure (24) which is open at two ends. The carrier structure includes at least one bar (16) extending helically around the longitudinal axis in such a way as to provide a helical primary shape (26) for the peripherally extending bar with more than one helical turn. Besides the helical primary shape (26) the bar has a zigzag-like or meander-shaped secondary shape (30) with reversal points and associated reversal portions (32), between which extend bar portions (34) of the peripherally extending bar with an extension component in the longitudinal direction of the stent. The carrier structure further includes connecting bars (40) which respectively bridge over a helical turn of the helical primary structure and which at their two longitudinal ends attach to the bar portions (34) of the helical primary shape between two respective adjacent reversal points.

10 Claims, 9 Drawing Sheets

STENT

The invention concerns a stent having a longitudinal axis and a peripheral wall which is formed at least over a part of the length of the stent by a lattice-like carrier structure which is open at two ends. That carrier structure includes at least one bar which extends in a helical configuration around the longitudinal axis in such a way as to provide a helical primary shape for the peripherally extending bar with more than one helical turn. In addition to the helical primary shape, the bar includes a zigzag-like or meander secondary shape. The carrier structure also has connecting bars which respectively bridge over a helical turn of the helical primary structure.

BACKGROUND OF THE ART

Stents in general are endovascular prostheses which are used, for example, in the treatment of stenoses. Stents are also known for treating aneurysms.

Stents basically involve a carrier structure which is suitable for supporting the wall of a vessel in an appropriate manner in order to expand the vessel or bridge over an aneurysm. For that purpose stents are introduced into the vessel in a compressed condition and then dilated or expanded at the location to be treated and pressed against the wall of the vessel. Such dilation can be effected, for example, by means of a balloon catheter. Alternatively, self-expanding stents are also known. They are made, for example, from a memory metal such as nitinol which, when a given jump temperature is reached, changes its shape, more specifically in the present case changing from the compressed form to the expanded form.

The desirable properties of a stent are embodied in many ways and in part in very different ways. Expandability of the stent which is as simple as possible is desired, as is ease of positioning thereof. In addition, in the case of balloon-expandable stents, elastic return (recoil) which is as slight as possible after expansion is desired so that the stent does not need to be expanded excessively beyond the desired size. An adequate carrier force is desired in the case of self-expanding stents and also in the case of balloon-expanding stents. In addition, in connection with drug-coated stents, there is a desire for the surface coverage of the vessel wall to be as uniform as possible. Finally, the stent should also involve a certain degree of flexibility about its longitudinal axis in order to suitably move with the vessel. That flexibility, however, should not be at the expense of the carrier force of the stent. The stent should also afford lateral branch accessibility that is as good as possible. In addition, attachment of bars of the carrier structure, so-called fishscaling, is generally undesirable. The list of the desirable properties set forth herein is far from being definitive.

The stent disclosed in U.S. Pat. No. 5,925,061 is also to be found among the many attempts to reconcile the desirable properties of a stent with each other. This US patent shows a whole series of stents of different configurations, inter alia, in FIGS. 6 through 10 a stent with a carrier structure which extends helically around the longitudinal axis of the stent is shown.

In spite of the large number of existing stent structures, there is still a need for the plurality of different desirable properties of a stent to be matched to each other as well as possible for a respective situation of use.

Accordingly, an object of the present invention is to develop a stent of the kind set forth in the opening part of this specification, in such a way that it affords a person skilled in the art a further option in terms of embodying its desirable properties.

SUMMARY OF THE INVENTION

In accordance with a preferred embodiment of the present invention, that object is attained by a stent of the kind set forth in the opening part of this specification, in which the connecting bars attach not to reversal portions of the secondary shape, but to bar portions of the helical carrier structure, which respectively extend between two reversal portions of the carrier structure and interconnect two adjacent reversal portions.

A stent of this kind differs in respect of its properties from the stents known from the state of the art, for example by virtue of its behaviour upon expansion, in particular with respect to possible changes in length. However, the stent also differs from the state of the art in that, while retaining other desirable properties, it affords advantageous surface coverage.

The stent is preferably cut, for example, by means of a laser out of a tubular initial workpiece.

Preferably, the material of the stent includes metals or alloys such as nitinol, titanium, tantalum or steel, for example high-quality steel 316 L. Alternatively, corrodable materials, in particular corrodable metals such as magnesium or iron can also be considered as the material for the stent. Cobalt-base alloys, nickel-base alloys, copper-base alloys and magnesium alloys may also be considered. Suitable titanium-tantalum alloys are $TiTa_{30}$, while suitable titanium-niobium alloys are $TiNb_{30}$. Alternatively, ADI-alloys on a palladium and silver basis or algiloy are also suitable. Thermoplastic materials also represent basically suitable materials, in particular bioresorbable thermoplastic materials.

The wall thickness of the tubular starting workpiece and thus the thickness of the bars produced by cutting is preferably substantially identical over the entire length and also over the periphery of the stent. Alternatively, the thickness of the bars in the region of the two ends of the stent may be reduced uniformly over the periphery of the stent, in relation to the bar thickness in the central region of the stent.

The term extension component, which is used to describe the geometry of the stent, means, in each case, the possible extension components in the longitudinal direction and the peripheral direction, respectively, of the stent. A bar which extends parallel to the longitudinal axis of the stent only has an extension component in the longitudinal direction of the stent. A bar which extends precisely in the peripheral direction of the stent only has an extension component in the peripheral direction and no extension component in the longitudinal direction of the stent. Bars extending inclinedly relative to the longitudinal axis of the stent and relative to the peripheral direction of the stent have extension components both in the longitudinal direction and also in the peripheral direction.

Two rounded-off reversal portions of the secondary shape, which are connected to a bar portion and which are thus immediately adjacent, delimit the respective portion, which is enclosed by those reversal portions, of the helical primary shape in the longitudinal direction of the stent.

In a preferred configuration, the bar portions connecting two adjacent reversal portions are not completely straight but are of a shallow S-shape, thus affording a shallow S-shaped tertiary form for the peripherally extending bar.

It is also preferable if the connecting bars are also not completely straight but are of a shallow S-shape.

The connecting bars preferably have a main extension component in the longitudinal direction of the stent. This means that the extension component in the longitudinal direction of the stent is greater than the extension component in the peripheral direction of the stent, so that the connecting bars preferably extend at a shallow angle relative to the longitudinal axis of the stent.

Preferably, a respective helical turn of the helical primary shape is bridged over by a plurality of connecting bars. Those connecting bars are preferably distributed as uniformly as possible over a helical turn. A preferred number of connecting bars per helical turn is between two and five.

In a preferred carrier structure having a plurality of helical turns, the helical turns are preferably bridged over by connecting bars in such a way that the connecting bars of adjacent helical turns are displaced or offset relative to each other in the peripheral direction of the stent.

In addition, the peripheral wall of the stent preferably has at least one end structure which adjoins an end face of the carrier structure and which forms a longitudinal end, which is open at its end face, of the peripheral wall. That end structure preferably includes a carrier portion which extends in an annular configuration around the stent in the peripheral direction thereof at the end thereof and from which the carrier structure branches, with the helical primary shape. The annular carrier portion is preferably formed by a peripherally extending bar which is of a wavy configuration in a meander-like or zigzag-like shape. Preferably, connecting bars are provided between the annular carrier structure and the first helical turns adjoining same.

BRIEF DESCRIPTION OF THE DRAWINGS

The invention will now be described in greater detail by means of an embodiment with reference to the Figures in which.

DETAILED DESCRIPTION OF THE INVENTION

Figure 1:
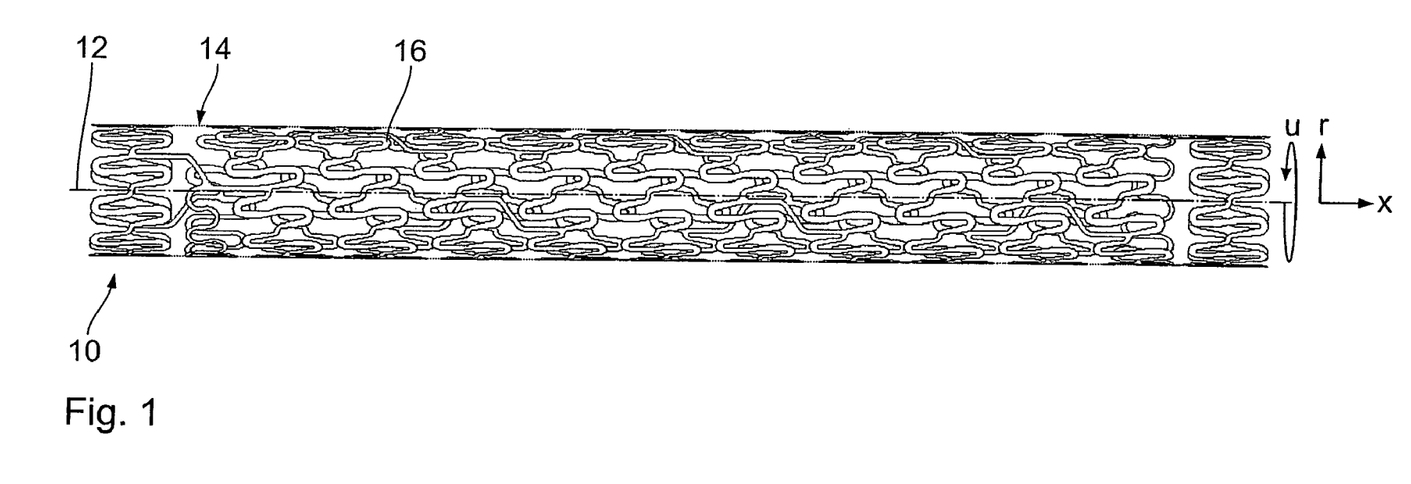
FIG. 1 shows a first embodiment of the stent with a lattice-like peripheral wall formed by bars.

FIG. 1 shows a stent 10 having a longitudinal axis 12 and a peripheral wall 14 which extends around the longitudinal axis 12 and which forms a carrier structure for the stent 10. The peripheral wall 14 and the carrier structure formed thereby are formed by bars 16.

The geometry of the peripheral wall 14 will be described by using the co-ordinates shown in FIG. 1, more specifically x as the longitudinal direction of the stent, r as co-ordinates extending radially with respect to the longitudinal direction x and u as co-ordinates extending in the peripheral direction of the stent 10.

Figure 2:
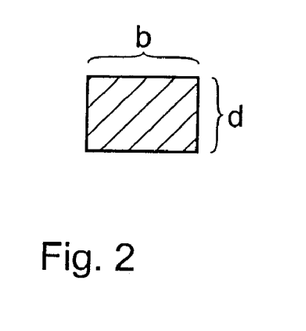
FIG. 2 is a view in cross-section through a bar.

It can be seen from the view in cross-section through a bar 16 as illustrated in FIG. 2 that the bar geometry can be described by a bar thickness d and a bar width b. In this case, the bar thickness d is the dimension of a bar in the radial direction r with respect to the stent while the bar width b represents the dimension of a bar in the direction of a peripheral surface formed by the peripheral wall 14.

Figure 3:
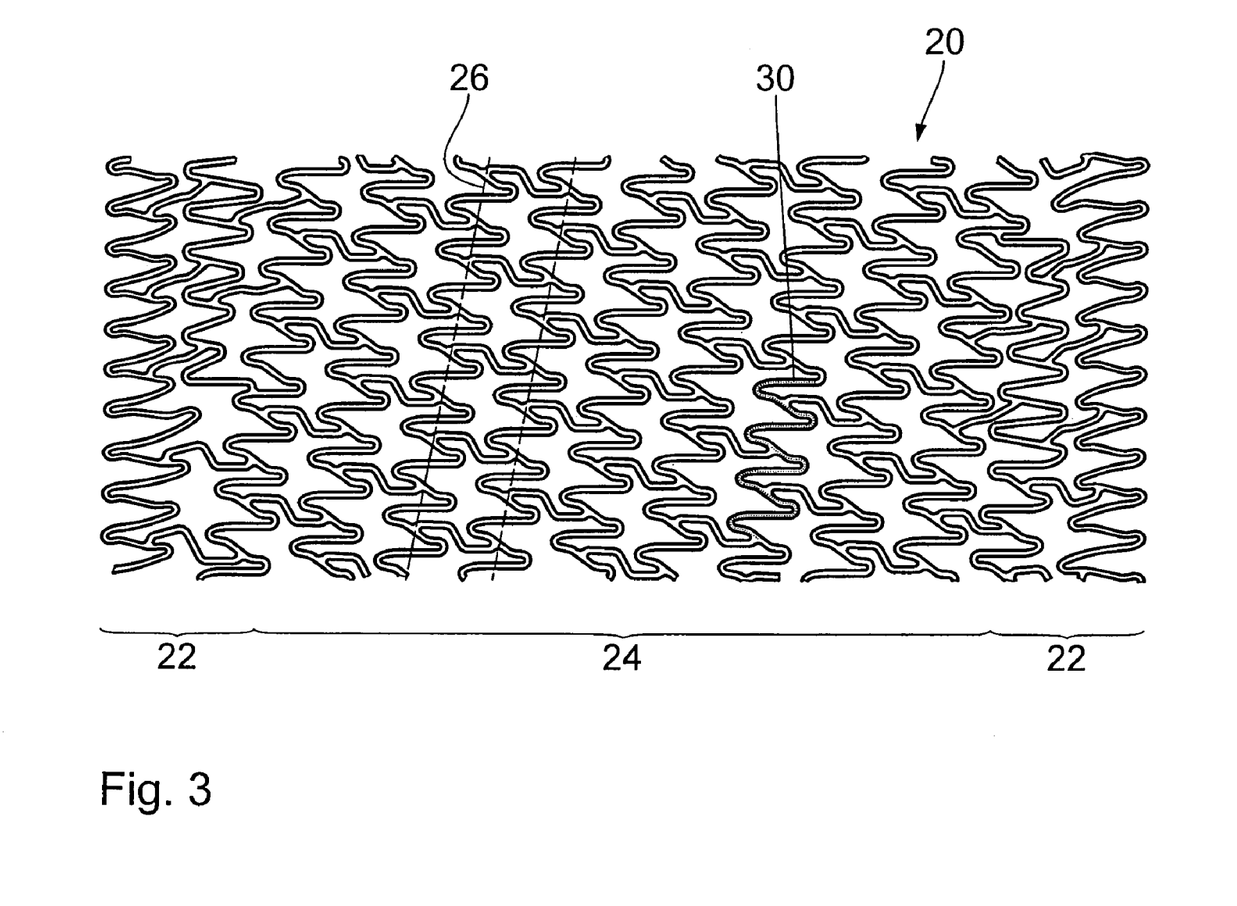
FIG. 3 shows a development of the peripheral wall of the stent shown in FIG. 1.

FIG. 3 shows a development 20 of the peripheral wall 14. It can be seen that the peripheral wall 14, at both longitudinal ends, has end structures 22 which enclose a central carrier structure 24.

Both the end structures 22 and also the central carrier structure 24 are formed by bars 16. They are preferably of the rectangular cross-section shown in FIG. 2, wherein the bar thickness d in relation to FIG. 3 corresponds to an extent perpendicularly to the plane of the drawing and the bar width b denotes the extent of a bar 16 in the plane of the drawing.

The central carrier structure 24 formed by the bars 16 is of a helical primary shape which is indicated by lines 26 in FIG. 3.

In addition, the bars 16 forming the central carrier structure 24 involve a secondary shape of a zigzag-shaped or meander-shaped form, as is illustrated in FIG. 3 by the dotted line 30.

Figure 4:
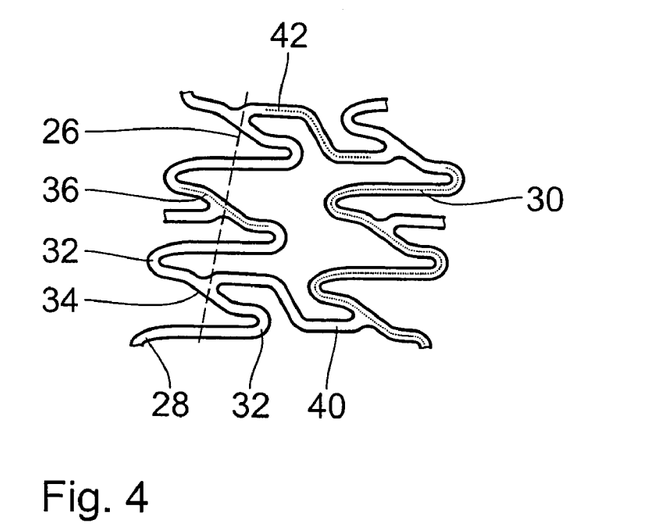
FIG. 4 shows a part on an enlarged scale of the development with a detail of the carrier structure.

FIG. 4 is a view on an enlarged scale of a portion of the central carrier structure 24. As can be seen from FIG. 4 the secondary shape of a zigzag-shape or meander shape is so oriented that the bars 16 have reversal points 32 between which extend respective bar portions 34, which have a main extension component in the longitudinal direction of the stent. In addition, the bar portions 34 involve a shallowly S-shaped tertiary shape, as is represented by the dotted line 36 in FIG. 4.

As can also be seen from FIGS. 3 and 4, besides the bars extending in a meandering helical configuration around the stent, the central carrier structure 24 also has connecting bars 40 that each bridge over a helical turn of the helical primary structure and which at their two longitudinal ends attach to the bar portions 34 of the helical primary shape between two respective adjacent reversal points. The connecting bars 40 are also preferably of a shallow S-shape which is indicated by the dotted line 42 in FIG. 4. As can be seen from FIG. 4, the connecting bars 40 have a main extension component in the longitudinal direction of the stent and extend at a shallow angle with respect to the longitudinal direction of the stent.

It can be seen from FIG. 3 that two adjacent helical turns of the central carrier structure 24 are preferably bridged over by between four and five connecting bars 40. In that arrangement the connecting bars 40 are so disposed that the connecting bars engaging on respectively different sides of a helical turn 26 are in mutually displaced or offset relationship in the peripheral direction of the stent.

Figure 5:
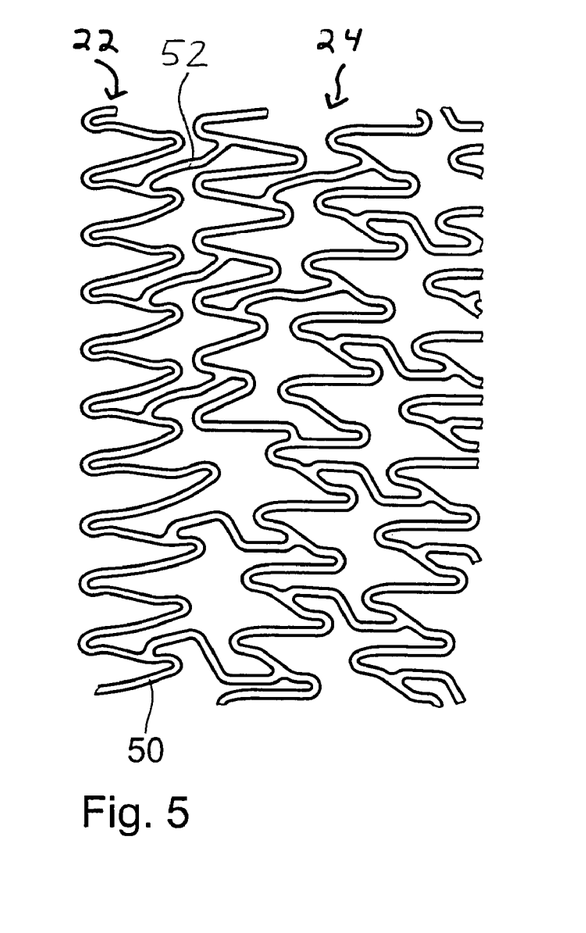
FIG. 5 shows a part on an enlarged scale of the development shown in FIG. 1 with the end structure of the stent.

FIG. 5 shows a view on an enlarged scale of an end structure of the stent. It will be seen that the longitudinal end of the peripheral wall is formed by a bar 50 which extends around the stent in an annular configuration and which is folded in a meander-like or zigzag configuration. The central carrier structure 24 is connected to the bar ring 50 by way of connecting bars 52. As part of the end structure 22 it can be considered that the outer helical turn of the central carrier structure 24, which in turn directly adjoins the ring bar 50, terminates by the corresponding bar portions becoming progressively shorter.

Figure 6:
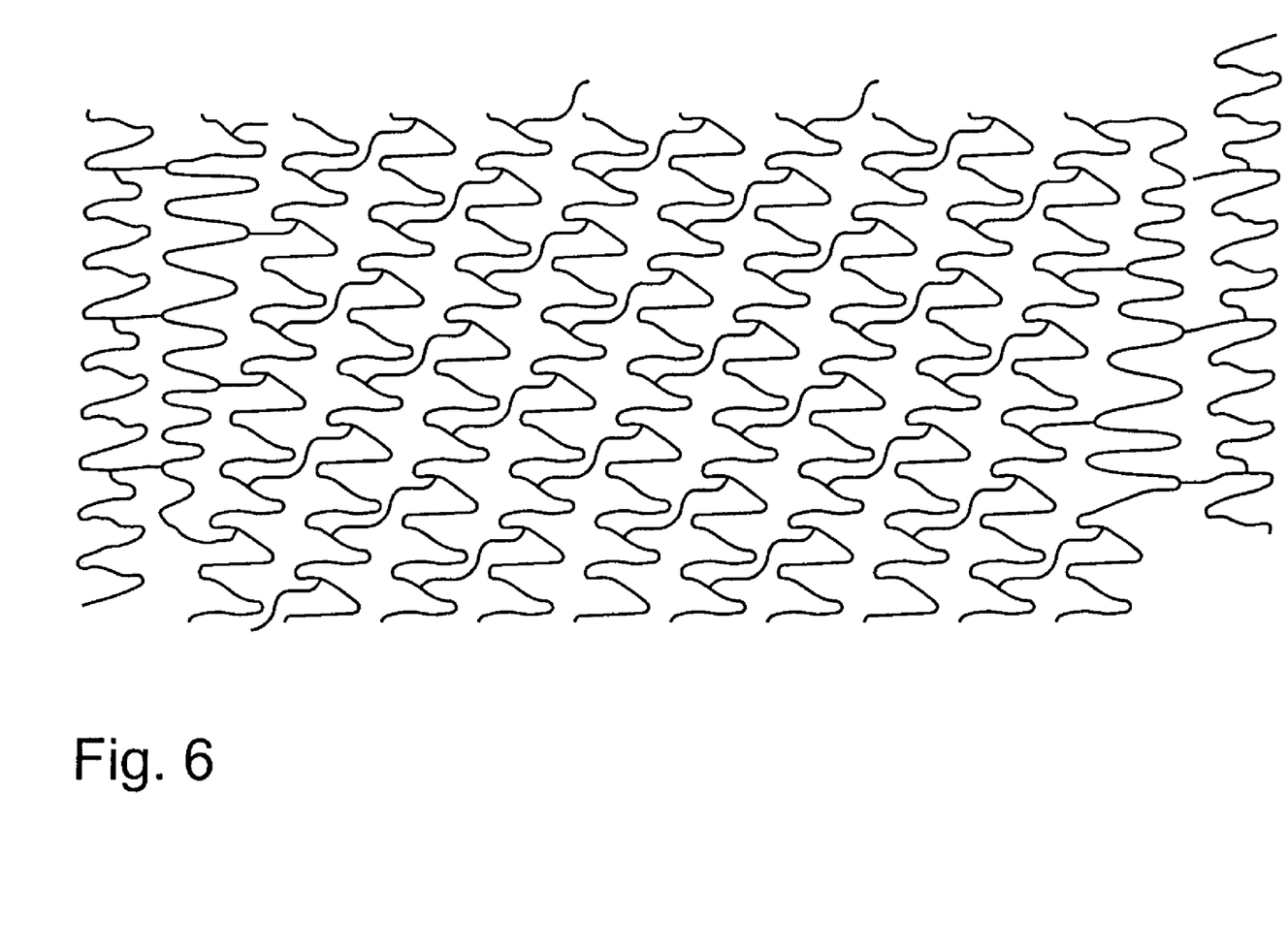
FIG. 6 shows an alternative embodiment of the stent.

FIG. 6 shows an alternative peripheral wall of a stent in the development which differs from the embodiment illustrated in FIGS. 1 through 5, in particular insofar as the connecting bars provided therein are arranged differently.

Figure 7:
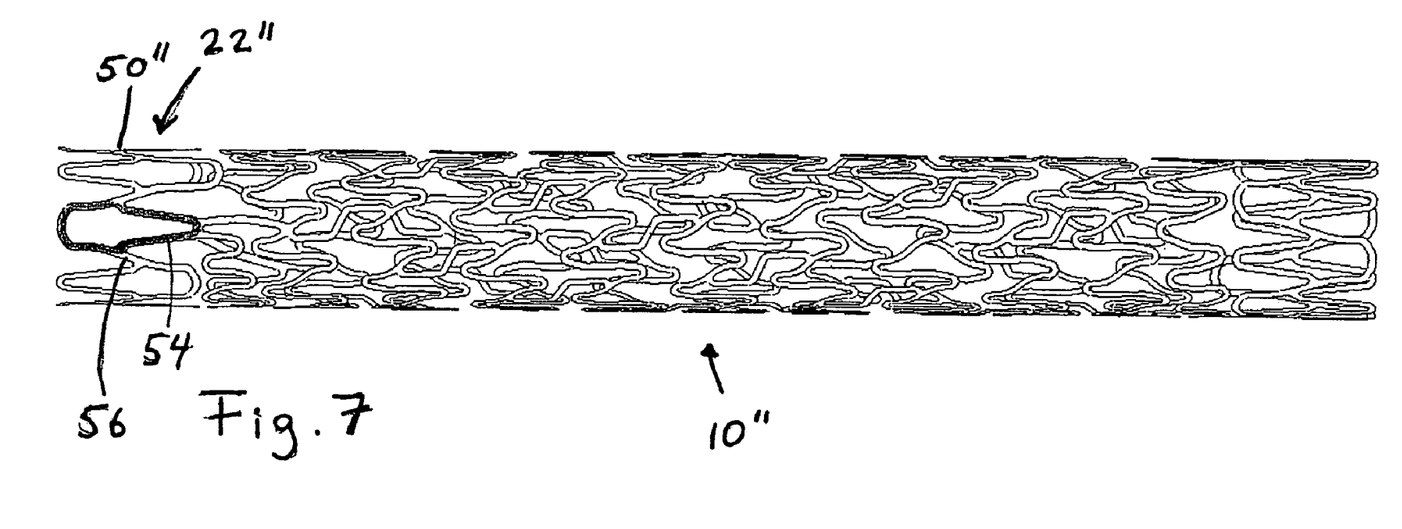
FIG. 7 shows a further alternative embodiment of a stent.

The stent 10" shown as a side view in FIG. 7 differs from stents shown in the preceding Figures in regard to the configuration of its end structure 22". End structure 22" is formed by a bar ring 50" which is formed by closed cells which are arranged in adjacent relationship in the peripheral direction of the stent 10" and of which a closed cell 54 is shown in dark lines in FIG. 7. Adjacent closed cells 54 are connected by peripheral connecting bars 56. An end structure 22" of this kind has advantageous properties in terms of the uniformity of the opening behaviour of the central carrier structure 24". Added to that is an advantageous behaviour in terms of the change in length of the stent 10" upon expansion thereof. In addition an end portion like the end portion 22", by virtue of its greater radial stability, has an advantageous effect on the collapsing pressure of the stent, that is to say on the forces which act radially on the stent and which the stent can withstand. Finally, the stent is better in terms of remaining adhered to a balloon catheter upon the insertion thereof.

Figure 8:
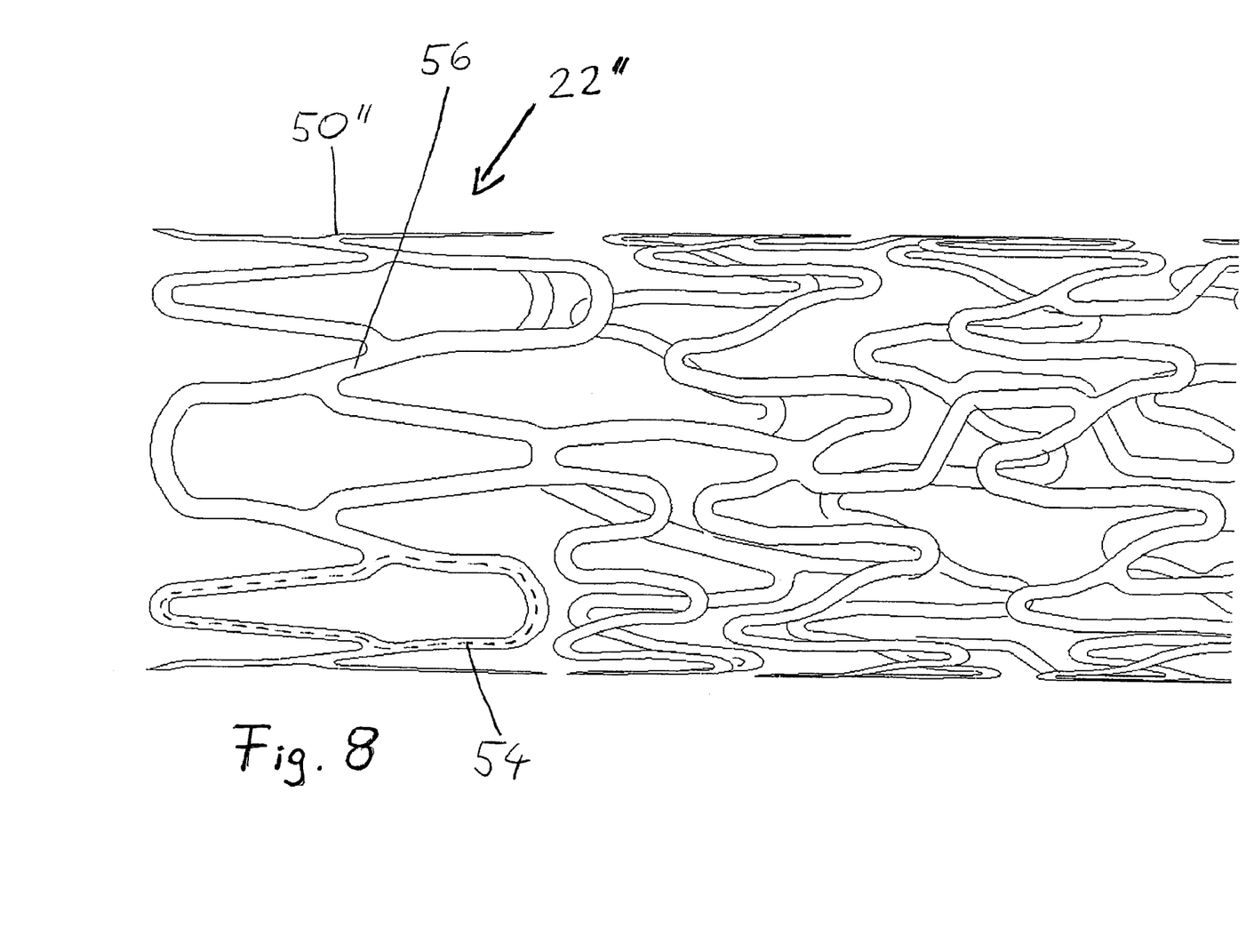
FIG. 8 shows a view on an enlarged scale of an end portion of the stent shown in FIG. 7.

FIG. 8 shows a view on an enlarged scale of the end portion 22" of FIG. 7.

Figure 9:
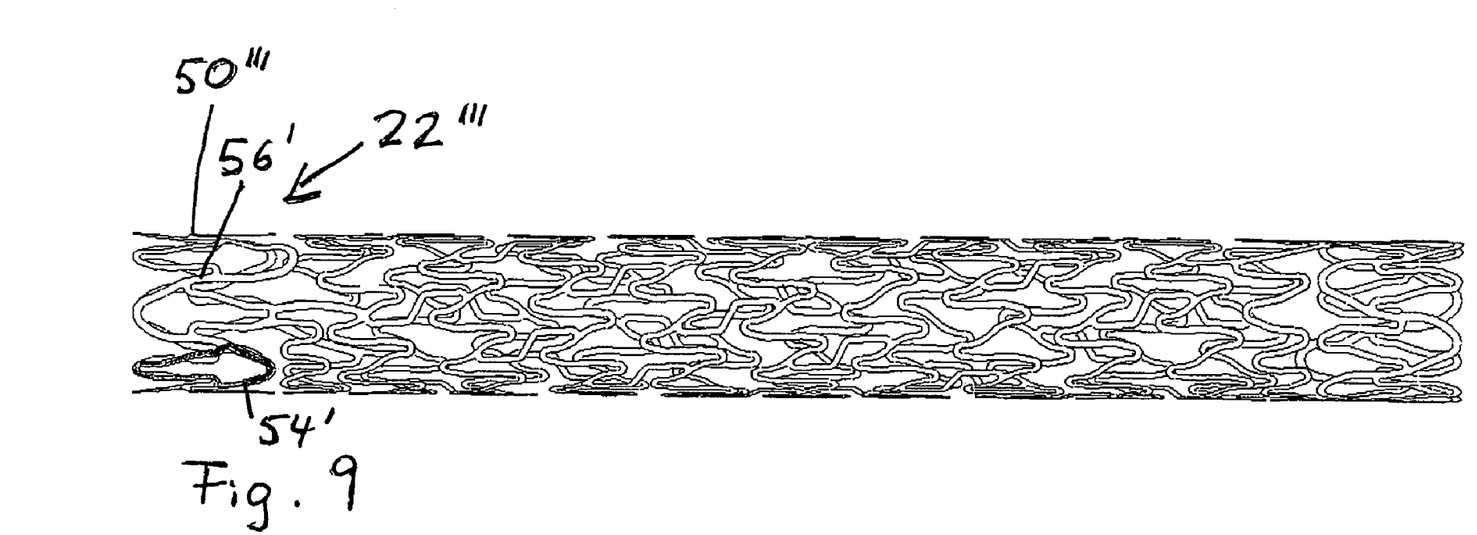
FIG. 9 shows a side view of a fourth variant of the stent.

The variant illustrated in FIG. 9 differs from that illustrated in FIG. 7 by virtue of the precise shape of the closed cells 54'.

Figure 10:
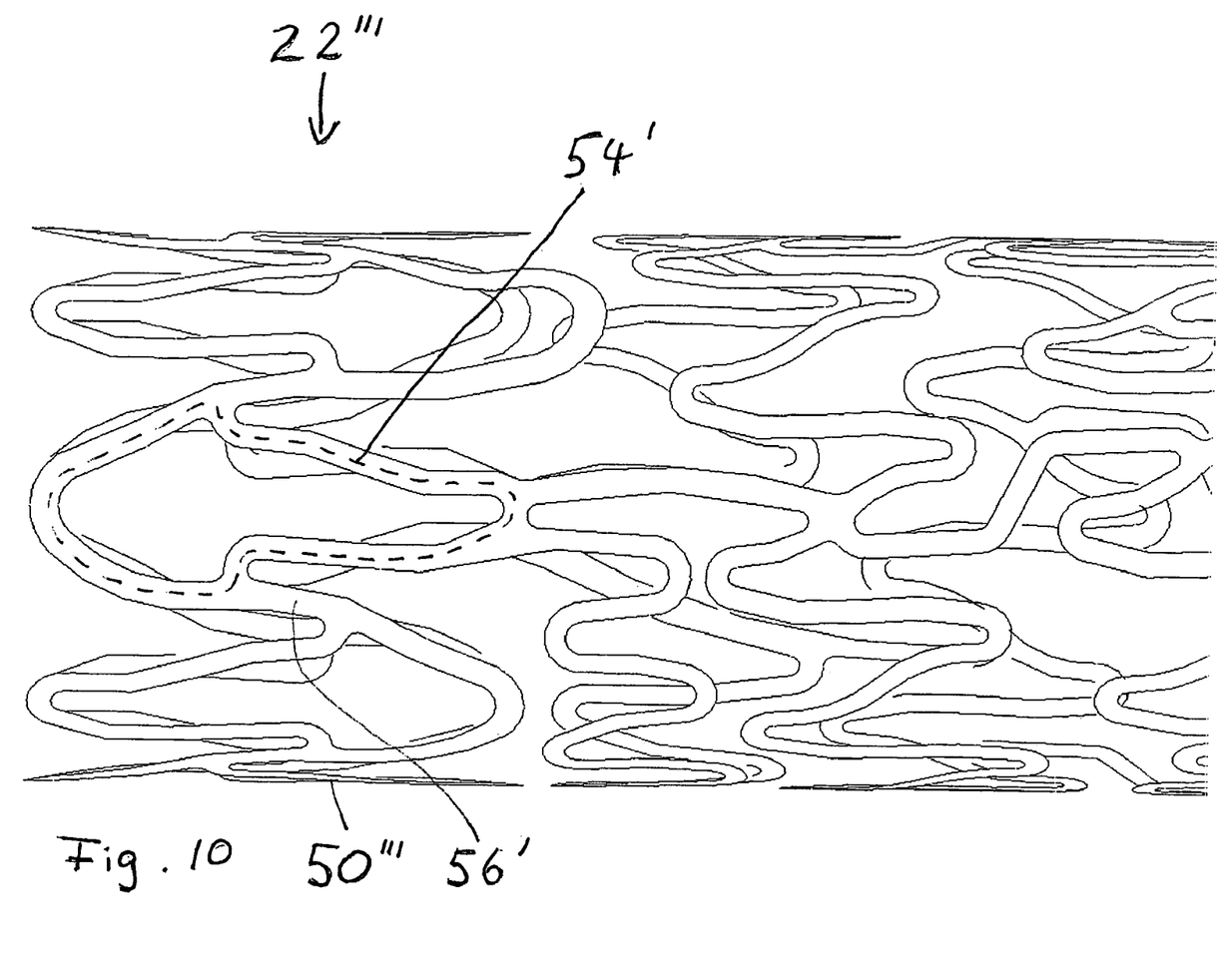
FIG. 10 shows a view on an enlarged scale of an end portion of the stent shown in FIG. 9.

FIG. 10 shows a view on an enlarged scale of the end portion 22'" shown in FIG. 9.

Figure 11:
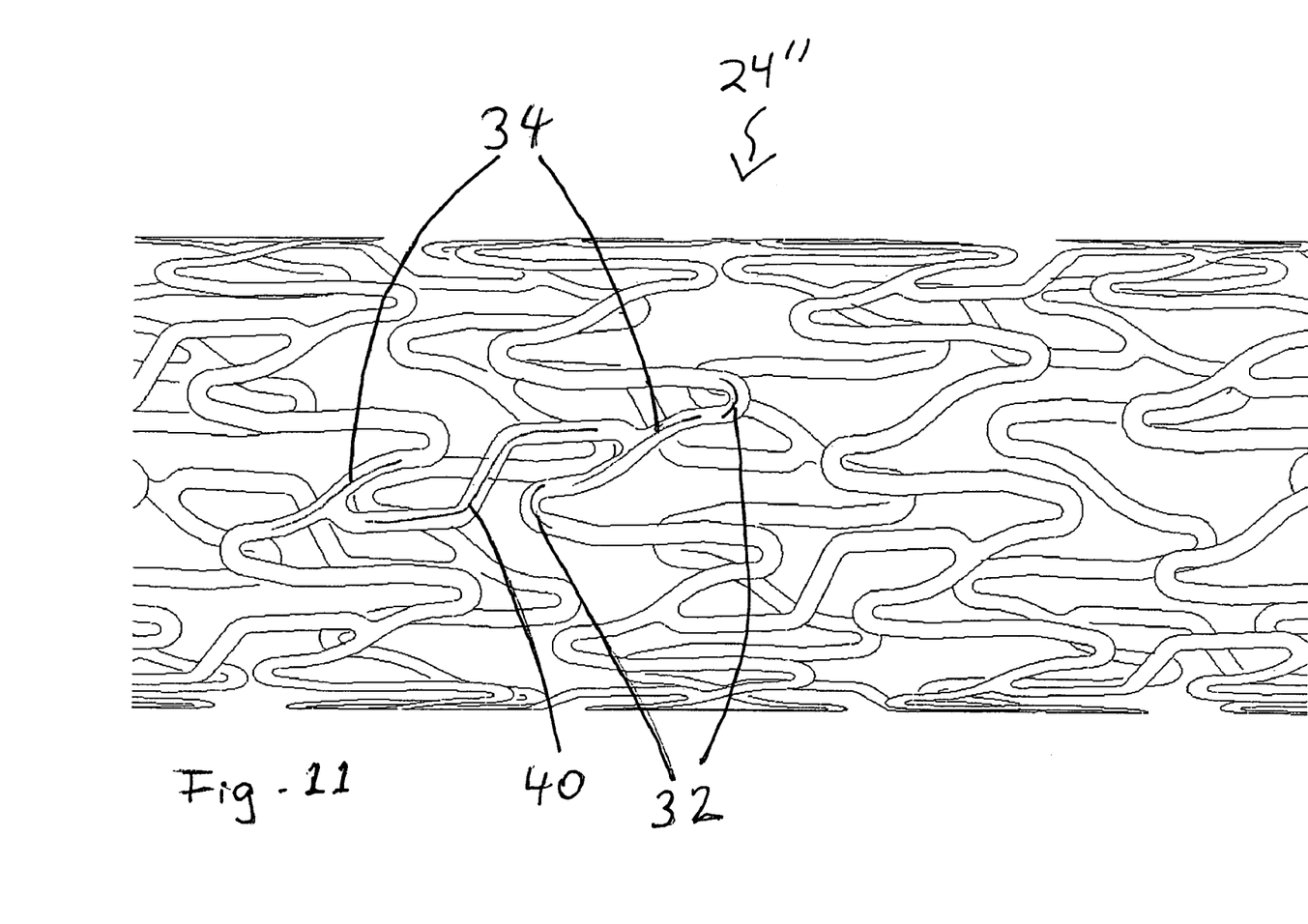
FIG. 11 shows a view on an enlarged scale of a central portion of the stent shown in FIGS. 7 through 11.

Finally FIG. 11 shows a view on an enlarged scale of a portion of a central carrier structure 24", as is common to the variants of the stents shown in FIGS. 7 through 10.

It cannot be seen from the Figures that the bars of the end structures 22 and the central carrier structure 14 can involve differing bar thicknesses d.

Suitable materials from which the carrier structures shown in the Figures can be made are specified in the preamble to the description. Depending on the respective situation of use involved, the illustrated peripheral walls may carry active substances which are bound to the peripheral wall of the stent, for example, by means of a polymer matrix applied to the peripheral wall.

What is claimed is:

1. A stent comprising:
   a longitudinal axis; and
   a peripheral wall,
   wherein the peripheral wall is formed at least over a part of the length of the stent by a lattice-like carrier structure which is open at two ends and which includes at least one bar extending helically around the longitudinal axis in such a way as to provide a helical primary shape for the peripherally extending bar with more than one helical turn,
   wherein the bar has a zigzag-like or meander-shaped secondary shape with reversal points and associated reversal portions, between which extend bar portions of the peripherally extending bar with an extension component in the longitudinal direction of the stent,
   wherein the carrier structure further includes connecting bars which respectively bridge adjacent helical turns of the helical primary structure and which at their two longitudinal ends attach to the bar portions of the helical primary shape between two respective adjacent reversal points,
   wherein the peripheral wall has at least one end structure which adjoins an end face of the carrier structure and which forms a longitudinal end, which is open at its end face, of the peripheral wall,
   wherein the bar portions adjacent to the end structure become progressively shorter approaching the terminus of the at least one bar; and
   wherein the end structure is formed by a bar ring formed by closed cells which are distributed over the periphery of the longitudinal end of the peripheral wall and which are connected together in pairs in the peripheral direction by way of peripheral connecting bars.

2. A stent as recited in claim 1, wherein the bar portions are of a shallow S-shape so as to afford a shallowly S-shaped tertiary shape of the peripherally extending bar.

3. A stent as recited in claim 1, wherein the connecting bars are of a shallow S-shape.

4. A stent as recited in claim 1, wherein the connecting bars have a main extension component in the longitudinal direction of the stent.

5. A stent as recited in claim 4, wherein the connecting bars extend at a shallow angle relative to the longitudinal axis of the stent.

6. A stent as recited in claim 1, wherein a respective helical turn is bridged by a plurality of connecting bars.

7. A stent as set forth in claim 6, wherein a respective helical turn is bridged by between 2 and 5 connecting bars which are substantially uniformly distributed in the peripheral direction over the helical turn.

8. A stent as recited in claim 7, wherein the carrier structure comprises a plurality of helical turns which are respectively bridged by connecting bars in such a way that the connecting bars of adjacent helical turns are displaced relative to each other in the peripheral direction of the stent.

9. A stent as recited in claim 6, wherein the carrier structure comprises a plurality of helical turns which are respectively bridged by connecting bars in such a way that the connecting bars of adjacent helical turns are displaced relative to each other in the peripheral direction of the stent.

10. A stent as set forth in claim 1, wherein the reversal portions are of a rounded configuration.

* * * * *